(12) United States Patent
Boki

(10) Patent No.: US 7,370,435 B2
(45) Date of Patent: May 13, 2008

(54) HANDHELD VAPORIZATION DEVICE

(75) Inventor: Gregoire Boki, 6082 Bossuet, Montréal, Québec (CA) H1M 2M9

(73) Assignee: Gregoire Boki, Montreal (CA)

( * ) Notice: Subject to any disclaimer, the term of this patent is extended or adjusted under 35 U.S.C. 154(b) by 0 days.

(21) Appl. No.: 11/351,260

(22) Filed: Feb. 10, 2006

(65) Prior Publication Data
US 2007/0186436 A1    Aug. 16, 2007

(51) Int. Cl.
F26B 25/06    (2006.01)
(52) U.S. Cl. ....................................... 34/235
(58) Field of Classification Search .................. 34/235
See application file for complete search history.

(56) References Cited
U.S. PATENT DOCUMENTS
6,089,857 A      7/2000   Matsuura et al.
6,164,287 A     12/2000   White
2004/0031495 A1  2/2004   Steinberg Primary Examiner—S. Gravini
(74) Attorney, Agent, or Firm—Venable LLP; Robert Kinberg; Amir R. Rohani

(57) ABSTRACT

A handheld vaporization device comprises a heating chamber for heating a substrate of volatile compound so as to yield vapor including the volatile compound. The heating chamber includes a closable opening, for example using a plug, to receive the substrate. The heating chamber also includes scavenging channels for allowing air to enter therein. The handheld vaporization device further comprises a vapor chamber mounted to the heating chamber so as to be in fluid communication therewith for receiving the vapor scavenged therefrom and has a vapor outlet for releasing the vapor including the volatile compound. By applying heat to the exterior of the handheld vaporization device's heating chamber, with a flame or any heating device, the confinement resulted from the heating chamber and the emissivity of its walls create a uniform heat across the substrate which is deposed into it. Heating the substrate in this manner permits great efficacy in extraction of undiluted organo-volatile elements.

38 Claims, 2 Drawing Sheets

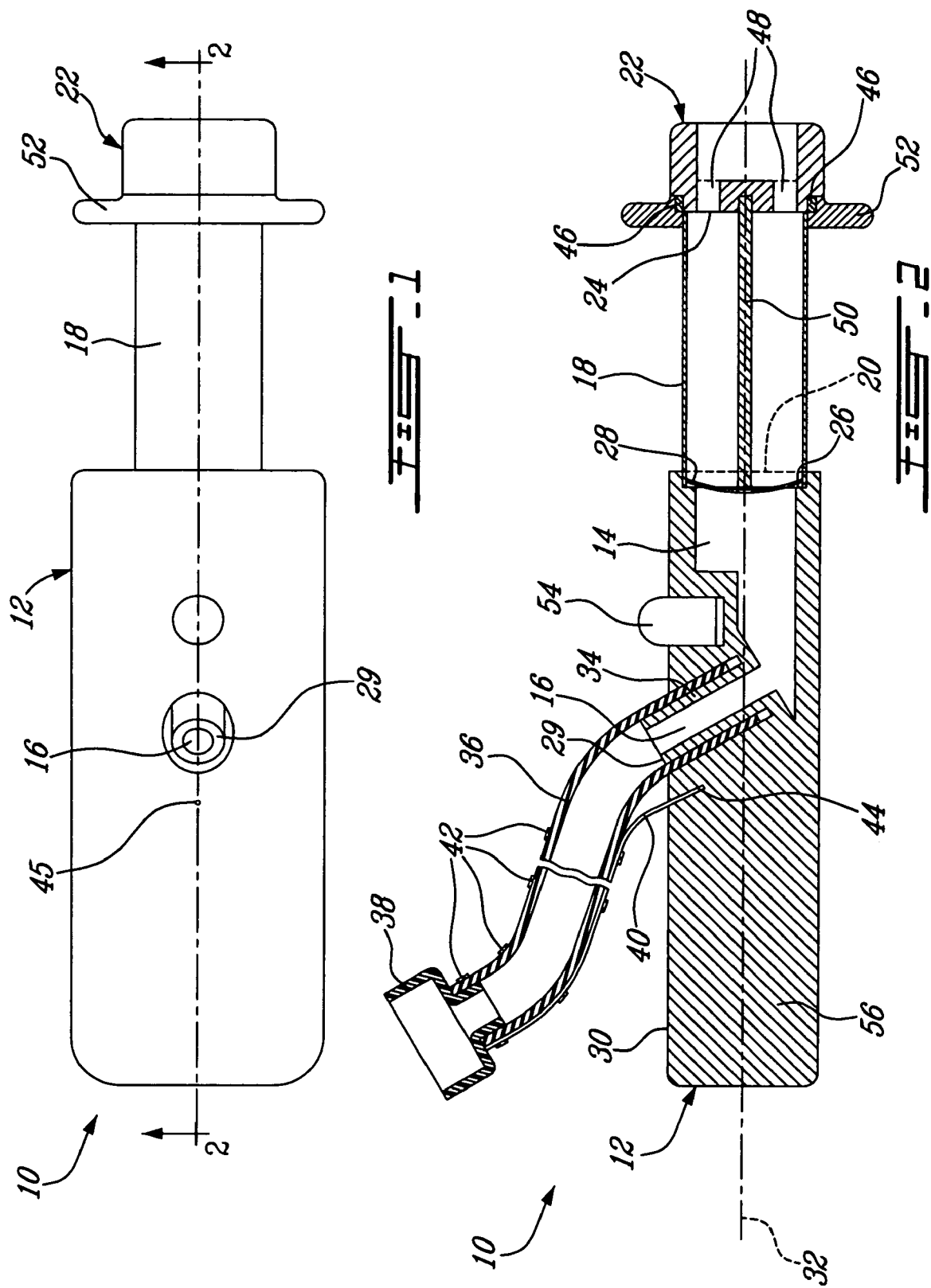

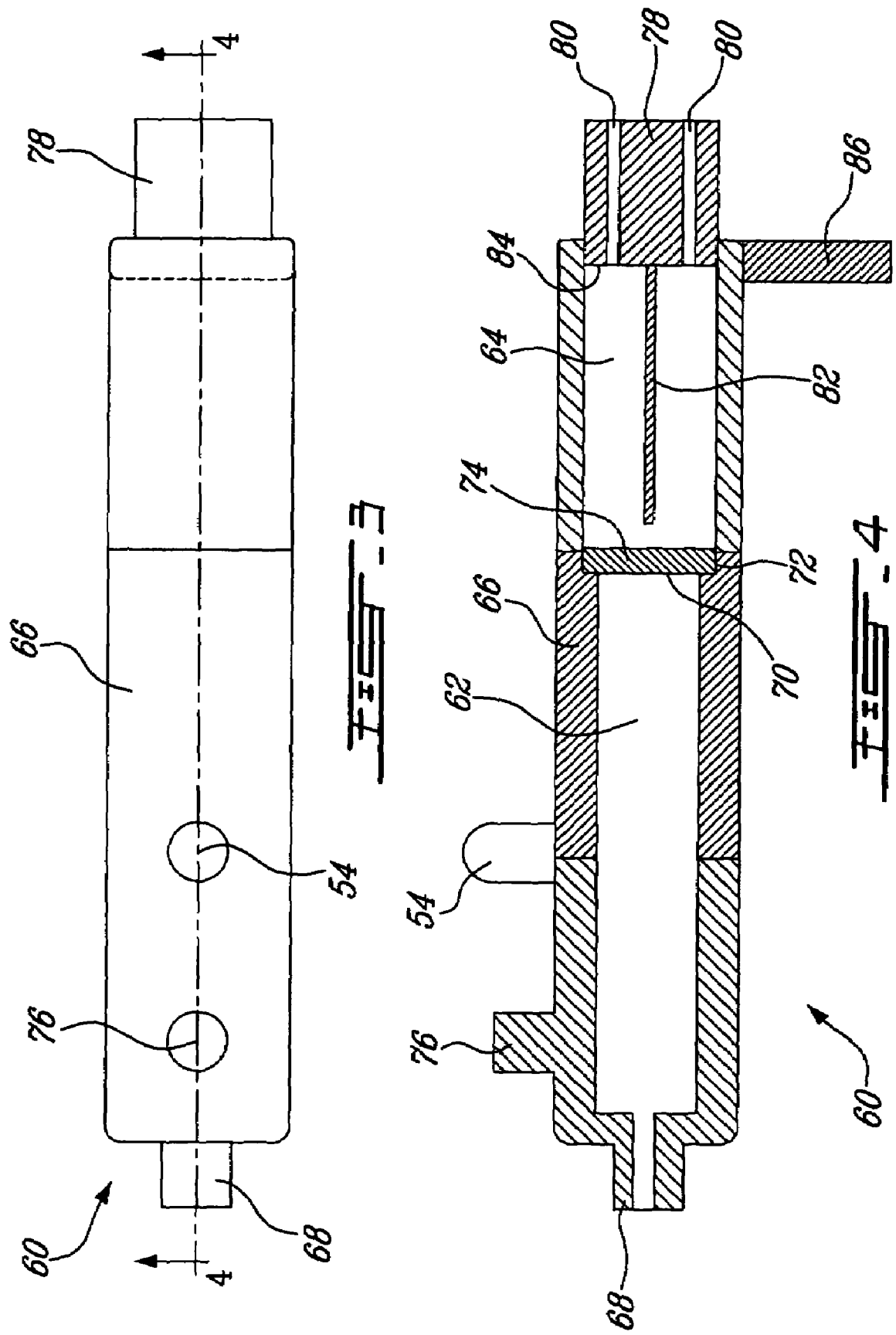

HANDHELD VAPORIZATION DEVICE

FIELD OF THE INVENTION

The present invention relates to heating and vaporization devices. More specifically, the present invention relates to a device for converting to a gaseous phase organo-volatile compounds contained in a substrate.

BACKGROUND OF THE INVENTION

Many means are presently known for converting a substrate of organo-volatile compounds into gaseous phase. These means can be divided into two categories.

A first type of device is based on the injection of a stream of hot air through the substrate to heat and vaporize organo-volatile compounds contained in it.

An example of such a device is described in United States Patent Application No. 2004/0031495 A1, published on Feb. 19, 2004 and naming Steinberg as the inventor.

A drawback of this type of device is that it tends to dilute the organo-volatile vapours into a stream of heating air.

A second type of device is based on the heating of a plate, onto which the substrate is deposited and heated thereon through one of its face.

A problem with these types of devices is that they only heat the substrate from a single side at a time.

OBJECTS OF THE INVENTION

An object of the present invention is therefore to provide improved method and system for converting to a gaseous phase organo-volatile compounds contained in a substrate.

Another object of the invention is to provide a portable system for converting to a gaseous phase organo-volatile compounds contained in a substrate.

SUMMARY OF THE INVENTION

More specifically, in accordance with the present invention, there is provided a handheld vaporization device comprising:

a heating chamber for heating a substrate of volatile compound enclosed therein so as to yield vapour including the volatile compound; the heating chamber including at least one scavenging opening and being openable to receive the substrate; and a vapour chamber mounted to the heating chamber so as to be in fluid communication therewith for receiving the vapour scavenged from the heating chamber and having a vapour outlet for releasing the vapour including the volatile compound.

By applying heat to the exterior of the handheld vaporization device's heating chamber, with a flame or any heating device, the confinement resulted from the heating chamber and the emissivity of its walls create a uniform heat across the substrate which is deposed into it. Heating the substrate in this manner permits great efficacy in extraction of undiluted organo-volatile elements.

Other objects, advantages and features of the present invention will become more apparent upon reading the following non restrictive description of illustrated embodiments thereof, given by way of example only with reference to the accompanying drawings.

BRIEF DESCRIPTION OF THE DRAWINGS

In the appended drawings:

FIG. 1 is a top plan view of a handheld vaporization device according to a first illustrative embodiment of the present invention;

FIG. 2 is a cross-section taken along line 2-2 from FIG. 1, the handheld vaporization device being illustrated with a tubing;

FIG. 3 is a schematic top plan view of a handheld vaporization device according to a second illustrative embodiment of the present invention; and FIG. 4 is a schematic cross-section taken along line 4-4 from FIG. 3.

DETAILED DESCRIPTION

A handheld vaporization device 10 according to a first illustrative embodiment of the present invention will now be described with reference to FIGS. 1-2.

The handheld device 10 comprises a first elongated body 12 having a cavity therein defining a vapour chamber 14, and a second elongated hollow body defining a heating chamber 18. The heating chamber 18 has a first longitudinal end opening 20 mounted to the vapour chamber 14 so as to be in fluid communication therewith and a second longitudinal end opening 24 closed by a plug 22. The first longitudinal end opening 20 of the heating chamber 18 defines a vapour exit and the second longitudinal end opening 24 defines a substrate deposite opening as will become apparent upon reading the following description.

Each of these components of the handheld vaporization device 10 will now be described in more detail.

The heating chamber 18 is configured for receiving and heating a substrate of organo-volatile compound (not shown). For that purpose, the heating chamber 18 is made of a heat resistant and thermally conductive material such as a ceramic and any metallic material including without limitations copper and silver. Indeed, as will be explained hereinbelow in more detail, heat is brought to the substrate by heating the outer surface of the heating chamber 18 using a flame or another heat source (not shown).

The heating chamber 18 can also be made of a composite heat resistant and conductive material. Also the heating chamber 18 can only be partly made of such a heat resistant and conductive material allowing bringing heat therein.

For example, the heating chamber 18 can be cylindrical, having a diameter of about 12 mm and a thickness of about 2 mm. Of course, since the handheld vaporization device 10 is to be portable, the heating chamber 18 can be made as compact as possible, such as for example having a volume less than about 20 $cm^3$. The dimensions of the heating chamber 18 are however sufficient to allow receiving a substrate.

The heating chamber 18 can also have other shapes and sizes, including a greater volume than 20 $cm^3$. Also, even though the heating chamber 18 is illustrated as having a regular cross section, it can also be provided with an irregular cross section.

The first longitudinal end 20 of the heating chamber 18 is mounted in the cavity 14 of the first elongated body 12. More specifically, the longitudinal end of the elongated body 12 adjacent the cavity 14 is provided with a shoulder portion 26 for receiving the first longitudinal end 20 of the chamber 18. The heating chamber 18 is secured to the first elongated body 12 using fastening means such as fasteners, glue, etc. The two bodies 12 and 18 can also be attached by press fitting, snuggly fitting, or by providing threads at their respective longitudinal ends, allowing screwing the heating chamber 18 in the cavity 14.

The first longitudinal end 20 of the heating chamber 18, which defines its vapour exit, is provided with a filter 28 for preventing solid particles coming from the substrate to exit through the vapour outlet 16 as will be explained hereinbelow in more detail.

Although the filter 28 is illustrated in FIG. 2 as being snuggly fitted in the heating chamber 18, it can be secured therein using other means. For example, shoulder portions can be provided in the heating chamber 18, wherein the filter 28 can simply be abutted thereon. The filter can also be secured at the interface between the two bodies 12 and 18.

It is to be noted that the filter 28 can also be mounted in the vapour chamber 14 anywhere between the first longitudinal end 20 of the heating chamber 18 and the proximate end 29 of the vapour outlet 16 so as to be upstream thereof.

The filter 28 can also be integral to the heating chamber 18, defining, for example, a perforated wall at the vapour exit end 20 of the heating chamber 18.

The vapour chamber 14 defined by the body 12 can be made of any material including polymeric resin, high performance polymeric material, composite material, ceramic material, metallic material, wood, etc, or any combination thereof.

The configuration and sizes of the vapour chamber 14 may vary.

The opening 16 in the first elongated body 12 defining the vapour outlet has a generally circular cross section. Although the opening 16 according to the first illustrative embodiment defines an acute angle with the body top surface 30 and with the longitudinal axis 32 generally defined by the device 10, it can also be perpendicular therewith. Also, the cross section of the vapour outlet 16 may have other cross-section than a circular one.

A tube guide 34, in the form of a small cylinder, is mounted in the vapour outlet 16 so as to protrude therefrom. The tube guide 34 allows receiving a flexible tubing 36 which is terminated by a flared end 38 that can act as a mouthpiece. The flexible tubing 36 with the flared end 38 allows canalizing of the vapour exiting from the vapour chamber 14 through the vapour outlet 16. In some application, it may also be used to facilitate its inhalation by a user. In operation, the flexible tubing 36 then allows safely putting some distance between the face of the user and the heat source (both not shown). The mouthpiece 38, flexible tubing 36 and tube guide 34 are tightly assembled to one another.

The position and configuration of the flexible tubing 36 can be adjusted via a deformable rod 40 which is attached to the flexible tubing 36 therealong. The rod 40 is secured along the tubing 36 using, for example, heat-shrinkable joints 42. The rod 40 can also be secured to the tubing 36 using other means, including without limitations clips (not shown), rubber bands (not shown), etc., The rod 40 can alternatively be inserted within the thickness of the tubing 36.

The distal end 44 of the rod 40 is received in a hole 45 practiced in the elongated body 12 adjacent the vapour outlet 16.

The position and configuration of the vapour outlet 16 may vary. The diameter and length of the tubing 36 may also vary. The tubing 36 may alternatively be directly connected in the vapour outlet 36 without being connected to a tube guide.

The tubing 36 can be made of any resilient material such as silicone, vinyl and ABS resin. The rod 40 is made of any semi-rigid hand-deformable material including metallic and polymeric materials.

The tubing 36 can also be made itself from a semi-rigid hand-deformable material.

The plug 22 is removably secured at the second longitudinal end 24 of the heating chamber 18 so as to selectively close the substrate deposite opening defined thereby.

The plug 22 is made for example of a polymeric resin. Other materials such as, without limitations, wood, polymeric, ceramic or metallic materials can also be used. The plug 22 is snugly fitted into the heated chamber 18. According to a further embodiment, it can also be snuggly fitted onto the heated chamber 18.

The plug 22 alternatively includes threads for screwing onto the peripheral edge of the cylinder 18.

Even though the handheld vaporization device 10 according to the first illustrative embodiment has been illustrated having its plug 22 positioned at the second longitudinal end opening 24 of the chamber 18, it can be positioned at any other position on the chamber 18 so as to allow temporary opening of the heating chamber 18 to deposit a substrate therein.

The plug 22 includes scavenging channels 48 for allowing air into the heating chamber 18 for scavenging the vapour produced therein out of the heating chamber 18 towards the vapour chamber 14.

It is to be noted that the present invention is not limited to a handheld vaporization device having scavenging channels positioned in the plug 22. The scavenging channels can be in the form of small openings in the heating chamber 18.

The plug 22 further comprises a cleaning rod 50 extending in the heating chamber 18 coaxially with the plug 22. The cleaning rod 50 is used to remove consumed substrate from the heating chamber 18 resulting from the operation of the handheld vaporization device 10.

The cleaning rod 50 is attached to the plug 22 by thread pressure, using glue or any other fastening means. The cleaning rod 50 can be made of any rigid material including without limitations wood or polymeric, metallic and ceramic materials.

The device 10 further comprises a flame gage 52 in the form of an annular collar 52 mounted to the heating chamber so as to extend outwardly therefrom. The flame gage 52 allows for visually indicating a preferential distance to the heating chamber 18 for keeping a heat source during heating of the heating chamber 18. A typical such preferential distance can be about 3 cm.

The flame gage 52 is made of a polymeric resin. It can also be made, without limitations, of wood, polymeric, ceramic, or metallic material.

According to the illustrated embodiment of FIGS. 1 and 2, the flame gage 52 is fastened to the heating chamber 18 using glue. Other fastening means, including fasteners can also be used. The flame gage 52 can also be made integral to the heating chamber 18.

Even though the flame gage 52 is illustrated in FIGS. 1 and 2 as an annular collar mounted to the heating chamber 18, it can take any form allowing indicating a preferential distance between a heat source (not shown) and the heating chamber 18. According to further illustrative embodiment, the flame gage 52 is secured to the cylinder first elongated body 12 or to the plug 22 for example.

The handheld vaporization device 10 further comprises a temperature monitor 54, mounted to the elongated body 12, for monitoring and controlling the temperature in the heating chamber 18 and for showing information indicative of said temperature. The temperature monitor 54 can take many forms including an electronic sensor with light and/or sound indicator. The temperature monitor 54 may be configured to indicate a precise temperature or a temperature range.

The temperature monitor 54 can alternatively be mounted to the heated chamber 18. In such a case, the temperature monitor 54 can be in the form of a well-known temperature-indicating paint or of a thermal stick applied onto the heated chamber 18 exterior wall.

The first elongated body 12 further defines a handle portion 56 for handling the handheld vaporization device 10.

In operation, a user removes the plug 22 to gain access to the substrate deposit opening 24 and inserts a substrate of organo-volatile compound into the heating chamber 18. The plug 22 is then put back in place to close the opening 24 of the heating chamber 18.

A heat source, such as a lighter (not shown), is used to heat the heating chamber 18 from the outside thereof. The flame gage 52 is used to determine the approximate position of the flame of the lighter from the heating chamber 18. In some applications, a user can then put the mouth piece 38 in or adjacent his or her mouth.

Heating of the heating chamber 18 causes the heating of the substrate therein, yielding a vapour which comprises the organo-volatile compound. The vapour is scavenged into the vapour chamber 14, passing through the filter 28, and then exits through the vapour outlet 16 and the tubing 36.

Turning now to FIGS. 3 and 4 of the appended drawings, a handheld vaporization device 60 according to a second illustrative embodiment of the present invention will be described. Since the handheld vaporization device 60 is similar to the handheld vaporization device 10, and for concision purposes, only the differences between the two embodiments will be described furthering.

The handheld vaporization device 60 comprises a vapour chamber 62 and a heating chamber 64 mounted to the vapour chamber 62 so as to be in fluid communication therewith. The vapour chamber 62 is defined by an elongated enclosure 66 having a first spout shape opening at its proximate end defining the vapour outlet 68 and a second opening 70 at its distal end. The distal end of the vapour chamber 62 includes a shoulder portion 72 to receive a filter 74 similar to the filter 28.

A tube guard 76 in the form of a clip protrudes from the top surface of the enclosure 66 near the proximate end thereof. The tube guard 76 allows attaching the flexible tubing (not shown) while in disuse.

A person skilled in the art will appreciate that the device 60 can be used without tubing, wherein the vapour exits the device 60 directly from the vapour outlet 68.

The temperature monitor 54 is secured to the top surface of the enclosure 66.

A plug 78, provided with scavenging channels 80 and a cleaning rod 82, is removably mounted in the distal end opening 84 of the heating chamber 64 in a press fitted way. The distal end opening 84 is thereby closable.

Finally, a flame gage in the form of a wall 86 is secured to the heating chamber 64 near the distal end thereof.

Even though the handheld vaporization devices 10 and 60 according to the first and second illustrative embodiment both include a heating chamber having a substrate deposit opening which can be closed using a plug, there is provided A handheld vaporization device according to a third illustrative embodiment of the present invention (not shown) similar to the handheld vaporization device 60 which includes a heating chamber having a substrate deposit opening located at the junction with the vapour chamber wherein the heating chamber is releasably mounted to the vapour chamber so as to allow access to the heating chamber to introduce a substrate. Of course, the heating chamber according to this third illustrative embodiment of the present invention also includes scavenging channels.

Moreover, the handheld vaporization device according to the present invention is not limited to a device including a heating chamber which requires to be heated using a remote heat source, such as a flame. Indeed, the heating chamber can be made or can include a material which can selectively generate heat. For example, the heating chamber may include one or more heating element which can be energized or activated for heating a substrate enclosed in the chamber.

Although the present invention has been described hereinabove by way of illustrated embodiments thereof, it can be modified, without departing from the spirit and nature of the subject invention as defined in the appended claims.

What is claimed is:

1. A handheld vaporization device comprising:
   a heating chamber for heating a substrate of volatile compound enclosed therein so as to yield vapour including said volatile compound, said heating chamber including walls made of thermally conductive material, the walls surrounding the substrate so as to transmit thereto heat from a heat source located outside the walls of the heating chamber relative to the substrate and applied to the walls, said heating chamber being openable to receive said substrate and including at least one scavenging opening; and
   a vapour chamber mounted to said heating chamber so as to be in fluid communication therewith for receiving said vapour scavenged from said heating chamber and having a vapour outlet for releasing said vapour including said volatile compound.

2. A handheld vaporization device as recited in claim 1, wherein said heating chamber further includes a substrate opening for receiving said substrate.

3. A handheld vaporization device as recited in claim 2, wherein said vapour chamber is mounted to said heating chamber via said substrate opening; wherein detaching said vapour chamber from said heating chamber allows access to said vaporization chamber for inserting said substrate therein.

4. A handheld vaporization device as recited in claim 2, wherein said heating chamber further comprises a plug for releasably closing said substrate opening.

5. A handheld vaporization device as recited in claim 4, wherein said at least one scavenging opening is located in said plug.

6. A handheld vaporization device as recited in claim 4, further comprising a cleaning rod secured to said plug.

7. A handheld vaporization device as recited in claim 4, further comprising a flame gage mounted to said plug for indicating a preferential distance for keeping the heat source from said heating chamber during heating of said heating chamber in operation.

8. A handheld vaporization device as recited in 7, wherein said flame gage is in the form of an annular collar.

9. A handheld vaporization device as recited in claim 1, further comprising a filter mounted in said handheld vaporization device, upstream from said vapour outlet for preventing solid particles coming from said substrate to exit through said vapour outlet.

10. A handheld vaporization device as recited in claim 1, wherein said heating chamber is made of at least one thermally conductive heat resistant material.

11. A handheld vaporization device as recited in claim 10, wherein said at least one thermally conductive heat resistant material includes at least one of a metallic material, a ceramic material and a composite material.

12. A handheld vaporization device as recited in claim 1, wherein said heating chamber is a cylindrical hollow body.

13. A handheld vaporization device as recited in claim 1, wherein said vapour chamber is defined by a cavity in a first body; said vapour outlet being defined by a first opening in said cavity.

14. A handheld vaporization device as recited in claim 13, wherein said cavity includes a second cavity opening; said heating chamber being in the form of an second elongated hollow body including first and second longitudinal ends; said first longitudinal end of said second elongated hollow body being mounted in said second opening of said cavity.

15. A handheld vaporization device as recited in claim 14, wherein said first longitudinal end of said second elongated hollow body is secured in said second opening of said cavity by a technique selected from the group consisting of press fitting, snugly fitting and screwing.

16. A handheld vaporization device as recited in claim 14, wherein said second longitudinal end of said second elongated hollow body defines a substrate opening for receiving said substrate; the handheld vaporization device further comprising a plug for releasably closing said substrate opening.

17. A handheld vaporization device as recited in claim 16, wherein said at least one scavenging opening is located in said plug.

18. A handheld vaporization device as recited in claim 16, further comprising a cleaning rod secured to said plug.

19. A handheld vaporization device as recited in claim 14, further comprising a filter mounted in second elongated hollow body for preventing solid particles coming from said substrate to exit through said vapour exit.

20. A handheld vaporization device as recited in claim 1, wherein said vapour outlet is in the form of a spout.

21. A handheld vaporization device as recited in claim 1, further comprising tubing secured to said vapour outlet so as to be in fluid communication therewith for orienting said vapour including said volatile compound.

22. A handheld vaporization device as recited in claim 21, wherein said tubing is terminated by a flared end.

23. A handheld vaporization device as recited in claim 21, wherein said vapour outlet includes a tube guide for receiving said tubing.

24. A handheld vaporization device as recited in claim 21, wherein said tubing is made semi-rigid by a deformable rod mounted to said tubing therealong.

25. A handheld vaporization device as recited in claim 24, wherein said deformable rod is secured to said tubing using at least one of shrinkable joints and clips.

26. A handheld vaporization device as recited in claim 1, further comprising a temperature monitor for monitoring and controlling a temperature in said heating chamber and for showing information indicative of said temperature.

27. A handheld vaporization device as recited in claim 26, wherein said temperature monitor is mounted to at least one of said heating chamber and said vapour chamber.

28. A handheld vaporization device as recited in claim 27, wherein said temperature monitor includes at least one of temperature-indicating paint and a thermal stick applied to said heating chamber.

29. A handheld vaporization device as recited in claim 26, wherein said temperature monitor includes at least one of an electronic sensor, a light indicator and a sound indicator.

30. A handheld vaporization device as recited in claim 1, further comprising a flame gage mounted to one of said heating chamber and said vapour chamber for indicating a preferential distance for keeping a heat source from said heating chamber during heating of said heating chamber in operation.

31. A handheld vaporization device as recited in claim 1, wherein said heating chamber is for heating from a remote heat source.

32. A handheld vaporization device as recited in claim 1, wherein said heating chamber includes at least one heating element.

33. A handheld vaporization device as recited in claim 1, wherein said heating chamber has a volume less than 20 $cm^3$.

34. A handheld vaporization device as recited in claim 33, further comprising a filter in said handheld vaporization device, upstream or directly in said heating chamber for preventing solid particles coming from said substrate to exit through said vapour outlet.

35. A handheld vaporization device as recited in claim 34, further comprising a temperature monitor for controlling temperature in said heating chamber.

36. A handheld vaporization device as recited in claim 34, further comprising a temperature monitor for showing information indicative of said temperature.

37. A handheld vaporization device as recited in claim 35, wherein said temperature monitor is further for showing information indicative of said temperature.

38. A handheld vaporization device as recited in claim 1, wherein said volatile compound is an organo-volatile compound.

* * * * *